United States Patent
Ikeda

(10) Patent No.: US 9,572,763 B2
(45) Date of Patent: Feb. 21, 2017

(54) WATER-IN-OIL EMULSION COMPOSITION

(71) Applicant: SHISEIDO COMPANY, LTD., Tokyo (JP)

(72) Inventor: Tomoko Ikeda, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 7 days.

(21) Appl. No.: 14/438,793

(22) PCT Filed: Oct. 28, 2013

(86) PCT No.: PCT/JP2013/079138
§ 371 (c)(1),
(2) Date: Apr. 27, 2015

(87) PCT Pub. No.: WO2014/069403
PCT Pub. Date: May 8, 2014

(65) Prior Publication Data
US 2015/0290114 A1 Oct. 15, 2015

(30) Foreign Application Priority Data

Oct. 30, 2012 (JP) ................................. 2012-239040

(51) Int. Cl.

| | |
|---|---|
| A61K 8/64 | (2006.01) |
| A61K 8/891 | (2006.01) |
| A61K 8/31 | (2006.01) |
| A61Q 1/02 | (2006.01) |
| A61Q 1/10 | (2006.01) |
| A61K 8/37 | (2006.01) |
| A61K 8/58 | (2006.01) |
| A61K 8/06 | (2006.01) |
| A61Q 5/06 | (2006.01) |
| A61K 8/894 | (2006.01) |
| A61Q 1/04 | (2006.01) |

(52) U.S. Cl.
CPC ................. *A61K 8/891* (2013.01); *A61K 8/06* (2013.01); *A61K 8/064* (2013.01); *A61K 8/31* (2013.01); *A61K 8/37* (2013.01); *A61K 8/375* (2013.01); *A61K 8/585* (2013.01); *A61K 8/894* (2013.01); *A61Q 1/02* (2013.01); *A61Q 1/04* (2013.01); *A61Q 1/10* (2013.01); *A61Q 5/06* (2013.01); *A61Q 5/065* (2013.01); *A61K 2800/52* (2013.01)

(58) Field of Classification Search
CPC ..................................................... A61K 8/064
See application file for complete search history.

(56) References Cited

U.S. PATENT DOCUMENTS

| | | |
|---|---|---|
| 6,426,079 B1 | 7/2002 | Tournilhac |
| 2011/0135585 A1 | 6/2011 | Ikeda et al. |
| 2012/0014895 A1 | 1/2012 | Ikeda et al. |
| 2013/0202543 A1 | 8/2013 | Kueper |

FOREIGN PATENT DOCUMENTS

| | | |
|---|---|---|
| JP | 2012131783 A2 | 7/2012 |
| WO | 2010016437 A1 | 2/2010 |
| WO | 2010113956 A1 | 10/2010 |
| WO | 2010149798 A2 | 12/2010 |

OTHER PUBLICATIONS

International Search Report dated Feb. 4, 2014 filed in PCT/JP2013/079138.
Araki, Hidefumi., "Silicone Shushoku Shibosan Sekken (SMFS) ni yoru Atarashii α Gel-kei to sono Skin Care eno Oyo," Fragrance Journal, 2009, vol. 37, No. 4, pp. 6-7.
Extended European Search Report dated Apr. 1, 2016 issued in the corresponding European patent application No. 13850887.4.

*Primary Examiner* — John S Kenyon
(74) *Attorney, Agent, or Firm* — Rankin, Hill & Clark LLP

(57) ABSTRACT

To provide a water-in-oil emulsion composition having a high stability and which provides fresh feeling in use and glossy finish. The water-in-oil emulsion composition of the present invention is characterized by comprising: (a) 1 to 20 mass % of a polyhydric alcohol fatty acid ester and/or a hydrocarbon; (b) 3 to 20 mass % of a transparent non-volatile silicone oil that separates when mixed with component (a) at 25° C.; (c) 0.1 to 5 mass % of zinc decyl trisiloxanecarboxylate; and (d) water.

7 Claims, 2 Drawing Sheets

Uniform layer | Separation

WATER-IN-OIL EMULSION COMPOSITION

RELATED APPLICATIONS

This application claims the priority of Japanese Patent Application No. 2012-239040 filed on Oct. 30, 2012, which is incorporated herein by reference.

FIELD OF THE INVENTION

The present invention relates to a water-in-oil emulsion composition and, in particular, to the improvement of feeling in use thereof.

BACKGROUND OF THE INVENTION

Generally, it is known that a water-in-oil emulsion composition widely used as a base for cosmetics increases in fresh feeling in use as the blending quantity of water increases. Moreover, viscosity increases as the internal-aqueous-phase increases and it tends to become stabilized as a composition. On the other hand, it is also known that incorporating a large amount of water to a water-in-oil emulsion composition is not easy and contrivance in the formulation is necessary.

Moreover, in a water-in-oil emulsion composition, various oil agents such as ester oil, silicone oil and hydrocarbon oil are used according to desired effects, and, in general, each property of these oils differ. Therefore, when two different oil agents are used in combination to obtain an emulsion composition having respective properties, it was not easy to maintain stability of the composition because of the separation of oil agents. The combination of oil agents which can be used in combination in a water-in-oil emulsion composition was limited.

Such problems in stability and the like of a water-in-oil emulsion composition that an aqueous phase and an oil phase are respectively related have been solved generally by combining highly compatible oil agents, or by gelling an oil phase that is a continuous-phase and suppressing fluidity and separation of the total composition.

PRIOR ART

Patent Literature

Patent literature 1: International unexamined patent publication No. WO2010/113956

DISCLOSURE OF THE INVENTION

Problem to be Solved by the Invention

It is known that silicone oil provides gloss to the skin as an oil agent. It is also known that silicone oil has an advantageous property in cosmetics that by combining silicone oil with an oil agent that is incompatible with silicone oil and rather adheres to the skin to exhibit its effect, silicone oil oozes out to the coating film surface and improves durability of makeup (for example, Patent literature 1). However, to provide them as a stable water-in-oil emulsion composition in a gel state (cream state) has not been achieved because it is a special combination of oil agents.

The present invention was made in view of the above-described conventional art. An object of this invention is to provide a water-in-oil emulsion composition that has high stability as a preparation, provides fresh feeling in use and glossy finish, and is excellent in durability of makeup.

Means to Solve the Problem

The present inventors have diligently studied to achieve the above-described object. As a result, the present inventors have found that an emulsion composition of an oil component, which contains specific oil agent and silicone oil, and water under blending of zinc decyl trisiloxanecarboxylate has a high stability as a preparation, provides fresh feeling in use and glossy finish and has long durability of makeup due to the oozing of silicone oil.

That is, the emulsion composition of the present invention is characterized by comprising:
(a) 1 to 20 mass % of a polyhydric alcohol fatty acid ester and/or a hydrocarbon;
(b) 3 to 20 mass % of a transparent non-volatile silicone oil that separates when mixed with component (a) at 25° C.;
(c) 0.1 to 5 mass % of zinc decyl trisiloxanecarboxylate; and
(d) water.

Furthermore, in the above-identified water-in-oil emulsion composition, it is preferable that component (a) is selected from polyglyceryl isostearate, glyceryl monoisostearate, pentaerythritol fatty acid ester and isostearyl glyceryl ether, wherein the addition mole number of glycerin is 4 to 10 and the number of isostearic acid residue is 1 to 4.

Furthermore, in the water-in-oil emulsion composition, it is preferable to further comprise a silicone surfactant having an HLB value of 7 or less.

Furthermore, the cosmetic of the present invention is characterized by comprising the above-described water-in-oil emulsion composition.

Furthermore, the makeup method of the present invention is characterized by comprising:
(I) applying a first agent containing a polyhydric alcohol fatty acid ester and/or a hydrocarbon and water; and
(II) applying a second agent containing a transparent non-volatile silicone oil that separates when mixed with (a) at 25° C. and zinc decyl trisiloxanecarboxylate on the applied surface after step (I).

Effect of the Invention

According to the present invention, a water-in-oil emulsion composition comprising two different types of oil components, having high stability, providing fresh feeling in use and glossy finish and is excellent in durability of makeup can be obtained.

BEST MODE FOR CARRYING OUT THE INVENTION

Figure 1:
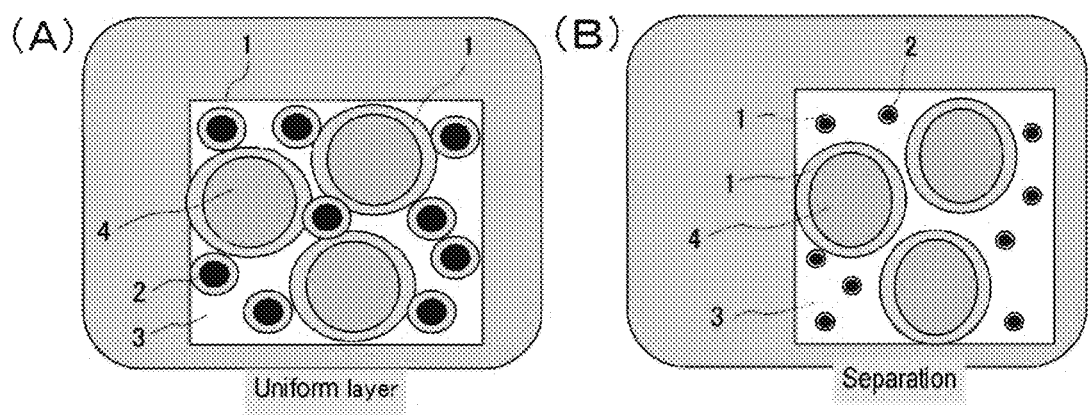
FIG. 1 shows the existing state of each constituent component in the water-in-oil emulsion composition of the present invention.

The emulsion composition of the present invention comprises: (a) a polyhydric alcohol fatty acid ester and/or a hydrocarbon, (b) a transparent non-volatile silicone oil that separates when mixed with component (a) at 25° C., (c) zinc decyl trisiloxanecarboxylate and (d) water.

In the following, each component is described in detail.

Component (a)

Component (a) is a polyhydric alcohol fatty acid ester and/or a hydrocarbon, and is an oil component that separates without dissolving when mixed with component (b) at ordinary temperature (25° C.). In the present invention, component (a) takes in coloring-materials to be an adhesion oil component at application and quickly separates with component (b), which is an oozing-out oil component. Therefore, it is preferable that component (a) is more excellent in dispersibility of coloring-materials, has higher affinity with the skin and has higher adhesion to the skin than component (b).

Examples of such polyhydric alcohol fatty acid ester include glycerin fatty acid ester such as glyceryl monopalmitate, glyceryl monostearate, glyceryl monoisostearate, glyceryl monooleate, glyceryl monolinoleate, glyceryl monobehenate, glyceryl monolaurate, glyceryl dipalmitate, glyceryl distearate, glyceryl dioleate, glyceryl dilinoleate, glyceryl dibehenate, glyceryl tristearate and glyceryl trioleate; polyglyceryl fatty acid ester such as diglyceryl monostearate, diglyceryl monooleate, diglyceryl dioleate, diglyceryl monoisostearate, polyglyceryl triisostearate, tetraglyceryl monostearate, tetraglyceryl monooleate, tetraglyceryl tristearate, tetraglyceryl pentastearate, tetraglyceryl pentaoleate, hexaglyceryl monolaurate, hexaglyceryl monomyristate, hexaglyceryl monostearate, hexaglyceryl monooleate, hexaglyceryl tristearate, hexaglyceryl tribehenate, hexaglyceryl pentastearate, hexaglyceryl pentaoleate, hexaglyceryl polyricinoleate, decaglyceryl monolaurate, decaglyceryl monomyristate, decaglyceryl monostearate, decaglyceryl monoisostearate, decaglyceryl monooleate, decaglyceryl monolinoleate, decaglyceryl distearate, decaglyceryl diisostearate, decaglyceryl tristearate, decaglyceryl trioleate, decaglyceryl pentastearate, decaglyceryl pentahydroxystearate, decaglyceryl pentaisostearate, decaglyceryl pentaoleate, decaglyceryl heptastearate, decaglyceryl heptaoleate, decaglyceryl decastearate, decaglyceryl decaisostearate and decaglyceryl decaoleate; pentaerythritol fatty acid ester such as pentaerythrityl tetra (behenate/benzoate/ethylhexanoate), pentaerythrityl tetra (ethylhexanoate/benzoate), dipentaerythrityl tripolyhydroxystearate, dipentaerythrityl hexa (hydroxystearate/stearate/rosinate), dipentaerythrityl (hydroxystearate/isostearate), dipentaerythrityl hexahydroxystearate, pentaerythrityl tetraethylhexanoate and pentaerythrityl tetraisostearate; sorbitan fatty acid ester such as trimethylolpropane fatty acid ester, sorbitan laurate, sorbitan palmitate, sorbitan stearate, sorbitan tristearate, sorbitan oleate, sorbitan trioleate, sorbitan behanate and sorbitan tribehenate; sucrose fatty acid ester such as sucrose monolaurate, sucrose monomyristate, sucrose monopalmitate, sucrose monostearate, sucrose monobehenate, sucrose monooleate, sucrose dipalmitate and sucrose distearate; propylene glycol fatty acid ester such as propylene glycol monolaurate, propylene glycol monopalmitate, propylene glycol monostearate and propylene glycol monooleate; and isostearyl glyceryl ether.

Among the above, in the present invention, it is preferable, in particular, to use polyglyceryl isostearate, glyceryl monoisostearate, pentaerythritol fatty acid ester and isostearyl glyceryl ether as component (a), wherein the addition mole number of glycerin as polyhydric alcohol is 4 to 10 and the number of isostearic acid residue as fatty acid is 1 to 4.

It is preferable that the above-described polyglyceryl isostearate is one which isotearic acid is added to a polyglycerin having an average addition mole number of 4 to 10 without specifying the position, and is a polyglycerin having an average addition mole number of 5. Moreover, it is preferable that isostearic acid is one which 2 to 4 moles, especially 3 moles, are added in one molecule. Therefore, in the present invention, it is especially preferable to use polyglyceryl-5 triisostearate.

The polyglyceryl isostearate may be provided by various known synthesis methods, but one with narrow distribution of the addition mole number of glycerin and which contains less cyclic compounds as impurities are preferable.

The polyglyceryl isostearate, for example, may be manufactured by methods described in Japanese patent No. 3487881 and Japanese unexamined patent publication No. 2006-111539 (a polyglycerin fatty acid ester obtained by the esterification of a fatty acid and a polyglycerin that has a hydroxyl value of 1200 or less and has 50% or more primary hydroxyl groups relative to all the hydroxyl groups).

For pentaerythritol fatty acid ester, especially pentaerythrityl tetra (behenate/benzoate/ethylhexanoate) and dipentaerythrityl hexahydroxystearate are preferable among the above-described examples.

As commercial products of the above, "SALACOS P-B822" manufactured by The Nisshin Oillio Group, Ltd. and "COSMOL 168M" also manufactured by The Nisshin Oillio Group, Ltd. can be listed and used preferably.

Examples of a hydrocarbon include oil agents that are semisolid or liquid at ordinary temperature (25° C.) such as liquid paraffin, heavy liquid isoparaffin, liquid isoparaffin, polybutene, hydrogenated polybutene, hydrogenated polyisobutene, hydrogenated polydecene, tetradecene, isohexadecane, isododecane, squalane, squalene, pristine, alpha-olefin oligomer and Vaseline. In particular, use of liquid paraffin and hydrogenated polyisobutene is preferable.

The blending quantity of component (a) is 1 to 20 mass % relative to the total amount of the emulsion composition, and preferably 2 to 15 mass %. When the blending quantity of component (a) is too large or too small, fresh feeling in use and glossy finish may be poor. Moreover, when the blending quantity is too large, stickiness after application tends to be generated.

Component (b)

Component (b) is a silicone oil that is transparent, separates without dissolving when mixed with component (a) at 25° C. and non-volatile at 25° C. After applying the emulsion composition of the present invention to the skin and the like, component (b) separates with component (a), forms a surface layer and improves especially the durability of makeup. In the present invention, the above-described component (b) should preferably exhibit a liquid state when viscosity is less than 500 mPa·s at 25° C. by a B-type viscometer.

In the present invention, the presence and absence of "separation" of component (a) and component (b) was measured under the following conditions.

(Measurement Condition)

Components (a) and (b) were used in a ratio of (a):(b)=1:1 (mass ratio), heated to 90° C. and mixed with stirring. Then, the mixture was allowed to stand to 25° C. When a boundary uniformly separated the mixture into two layers, it was denoted as "separated". When it was a translucent state or a transparently miscible state without a boundary, it was denoted as "not separated". Furthermore, when two or more types of silicone oils are used as component (b), the presence and absence of separation differ with their blending ratios.

Therefore, the presence and absence of separation needs to be confirmed according to the blending ratio of component (b).

Examples of a silicone oil as the above-described component (b) include dimethylpolysiloxane; methylhydrogenpolysiloxane; methylphenyl silicone such as trimethylpentaphenyltrisiloxane, diphenyldimethicone, diphenylsiloxyphenyltrimethicone, phenyltrimethicone and phenyldimethicone; and perfluorooctylethyl/diphenyldimethycone.

These silicone oils may be used in combinations of one or more types according to form of use of the water-in-oil emulsion composition of the present invention. For example, when the present invention is used in foundations, use of dimethylpolysiloxane is preferable, and when it is used in lipsticks, use of diphenyldimethicone and trimethylpentaphenyltrisiloxane is preferable.

The blending quantity of component (b) is 3 to 20 mass % relative to the emulsion composition, and preferably 5 to 15 mass %. If the blending quantity of component (b) is less than 3 mass %, there will be no gloss in finish and the durability of the coating film will be lower. If the blending quantity of component (b) is more than 20 mass %, the stability of the composition tends to be lower.

Component (c)

Component (c) is zinc decyl trisiloxanecarboxylate which is a metal salt (metal soap) of a carboxy-modified silicone.

A method for obtaining zinc decyl trisiloxanecarboxylate used in the present invention is not particularly limited. As a synthesis method, mixing
(A) a composition containing a compound represented by the following general formula (I),

[Formula 1]

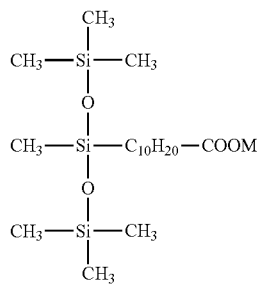

(In the formula, M represents a hydrogen atom or a monovalent metal atom)
(B) an aqueous solution containing zinc ion ($Zn^{2+}$), and
(C) an aqueous solution containing hydroxide ion
may be an example.

In the above-described general formula (I), M represents a hydrogen atom or a monovalent metal atom. Examples of the monovalent atom include Li, Na and K.

The above-described component (A) may be obtained by a known synthesis method. For example, such as a method comprising; addition-reacting 1,1,1,3,5,5,5-heptamethyltrisiloxane and carboxylic acid trimethylsilyl derivative having a vinyl terminal in the presence of a platinum catalyst, and deprotecting by alcoholysis by adding at least 1 mole or more of a monovalent alcohol per 1 mole of trimethyl group, which is the protecting group, water or a mixture thereof for heating. Furthermore, commercial products may be used.

Examples of component (B) include aqueous solution such as zinc chloride, zinc sulphate, zinc nitrate, zinc phosphate, zinc hydroxide and the like. Examples of component (C) include an aqueous solution such as sodium hydroxide, potassium hydroxide, calcium hydroxide, magnesium hydroxide, barium hydroxide, zinc hydroxide, aluminum hydroxide, iron hydroxide, copper hydroxide and the like.

When the above-described component (A) is added to component (B) (an aqueous solution), a specific functional group part, which is an active part, will have property of an anion and the specific functional group part forms a metal soap by reacting with polyvalent metal cation ionized from component (B). Zinc decyl trisiloxanecarboxylate is formed by neutralizing this metal soap with component (C).

Synthesis examples of zinc decyl trisiloxanecarboxylate are described below, however, the present invention is not limited thereto.

<Synthesis Example 1>

1400 g of 1% sodium hydroxide (NaOH) solution was prepared in a flask equipped with a stirrer, a thermometer and a cooling pipe, and heated to 70° C. 145.5 g of compound α obtained by the below-described synthesis method was added at 70° C. and mixed with stirring for 1 hour while maintaining the temperature. Then, 231.6 g of 25% zinc sulphate heptahydrate ($ZnSO_4 \cdot 7H_2O$) solution was added at 70° C., mixed with stirring for 1 more hour and deposited a zinc soap. 65.1 g of 5% sodium hydroxide solution was added thereto and mixed with stirring for 1 hour at 70° C. After confirming that it is neutral (completion of the neutralization reaction), it was cooled and water was removed. The obtained product was heated and dissolved in an excess amount of ion-exchanged water. Separation of water was performed 5 times, and zinc hydroxide and by-produced salt ($Na_2SO_4$) were washed.

Then, the product was dried at 105° C. under reduced pressure, and a transparent to white solid substance was obtained. As a result of an analysis, the above-described substance contained a complex salt composition represented by "$R^{Si}$—$C_{10}H_{20}$—$COO^-(Zn^{2+})_{5/8}(OH^-)_{1/4}$" as an average composition formula, when a part originating from compound A was abbreviated as "$R^{Si}$—$C_{10}H_{20}$—$COO^-$".

The neutralization reaction formula is as follows.

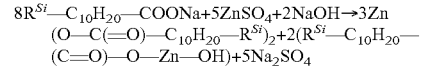

(Synthesis Method of Compound α)

100 g of 1,1,1,3,5,5,5-heptamethyltrisiloxane and 0.02 g of toluene solution of a platinum-1,3-divinyl-1,1,3,3-tetramethyldisiloxane complex were added to a flask equipped with a stirrer, a reflux condenser, a dropping funnel and a thermometer. While the temperature was kept within the range of 70 to 100° C., 105 g of trimethylsilyl undecylenate was added dropwise to the flask. After the completion of the dropwise addition, the mixture was aged at 100° C. for 2 hours, and the completion of the reaction was then confirmed using a gas chromatography. Low-boiling point fractions were distilled off under reduced pressure. Then, methanol and water were added thereto, and the mixture was aged for 5 hours under reflux for deprotection. Then, low-boiling point fractions were removed again under reduced pressure to obtain Compound α. As a result of an analysis, Compound α was confirmed to be represented by the chemical structural formula shown below.

[Formula 2]

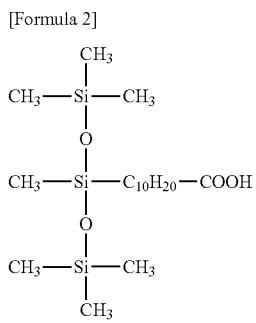

The blending quantity of component (c) is 0.1 to 5 mass % relative to the emulsion composition, and preferably 0.5 to 3 mass %. If the blending quantity of component (c) is less than 0.1%, the stability of the composition may be insufficient, and if it is more than 5 mass %, the feeling in use and the effect of finish of the composition may be poor.

Component (d)

Component (d), which is water, is a component constituting an internal-aqueous-phase of a water-in-oil emulsion composition, and it may contain an aqueous component which can be blended to an aqueous-phase. The blending quantity of the water is not particularly limited unless it is within the range that the effect of the present invention is not impaired. When a composition in a gel state (cream state) that is more excellent in freshness is to be obtained, the internal-aqueous-phase proportion is preferably 40 mass % or more relative to the component, more preferably 40 to 90%, and still more preferably 45 to 90 mass %. The above-described blending quantity corresponds to the blending quantity of the total internal-aqueous-phase consisted of water and an optional aqueous component.

Moreover, in the emulsion composition of the present invention, it is preferable that a silicone surfactant is blended as an emulsifying agent, especially dimethyl polysiloxane which has introduced polyoxyalkylene group or polyglycerol group. The HLB (Hydrophile-Lipophile-Balance) value of the above-described emulsifying agent is 7 or less.

Examples of such silicone surfactant include PEG-3 dimethicone, PEG-9 methylether dimethicone, PEG-10 dimethicone, PEG-9 polydimethylsiloxyethyl dimethicone, lauryl PEG-9 polydimethylsiloxyethyl dimethicone, PEG/PPG-20/22 butyl ether dimethicone, polyglyceryl-3 disiloxane dimethicone, polyglyceryl-3 polydimethylsiloxyethyl dimethicone, lauryl polyglyceryl-3 polydimethylsiloxyethyl dimethicone and the like. In the present invention, PEG-10 dimethicone and lauryl PEG-9 polydimethylsiloxyethyl dimethicone are preferable, and PEG-10 dimethicone is more preferable.

The blending quantity of the above-described emulsifying agent is not particularly limited, however, use of about 0.05 to 1.0 mass % is preferable in general.

The water-in-oil emulsion composition of the present invention exhibits a glossy finish as an oil agent and improves the durability of the coating film, namely, the durability of makeup by separating two incompatible oil components, which are component (a) and component (b), and thereby forming a surface layer (a transparent layer) and an adhesion layer respectively when it is applied to the skin and the like at ordinary temperature (25° C.). On the other hand, each of the above-described oil agent needs to be dispersed uniformly in the composition and maintained integrally until composition is applied to the skin to maintain the stability as a water-in-oil emulsion composition.

In addition, the emulsion of the present invention may obtain fresh feeling in use at application by blending water, which is component (d), together with the effect of the above-described oil components. However, if only components (a) and (b), which are the oil components, and component (d) are merely emulsified, the high fluidity of water may prevent stable dispersion of the two oil components and make them separate within the composition.

Therefore, the present inventors decided to use zinc decyl trisiloxanecarboxylate, which is component (c), to maintain the state that the above-described two oil components and water are stably and uniformly dispersed within the composition respectively.

FIG. 1 is a schematic diagram showing the existing state of components (a) to (d) in the emulsion composition of the present invention. When the composition of the present invention is prepared, zinc decyl trisiloxanecarboxylate, which is component (c), incorporates water or component (a) (in FIG. 1, polyglyceryl triisotearate) which is associated with water to form lamella, and they introduce a system that is dispersed to a continuous phase of component (b) as emulsifying particles (FIG. 1 (A)).

In the above-described system, the emulsifying particles (component (d) and lamella of component (d) and component (a)) that are incorporated by component (c) hardly separate or unite as they are densely filled in the continuous phase and hardly move physically. Therefore, the emulsion composition of the present invention apparently exhibits a stable uniform layer system having a property of a gel that does not flow.

FIG. 1 (B) shows the state that water, which is component (d), has volatized from the structure of FIG. 1 (A). When water volatizes, the emulsifying particles containing component (a) will become movable, and the fluidity of the composition is generated. Thus, component (a) and (b), which are originally incompatible, start to separate respectively and form the adhesion layer and the surface layer which are described above. Component (c) which has incorporated water is confirmed to be transferred to the surface layer with component (b) after volatilization of water.

Figure 2:
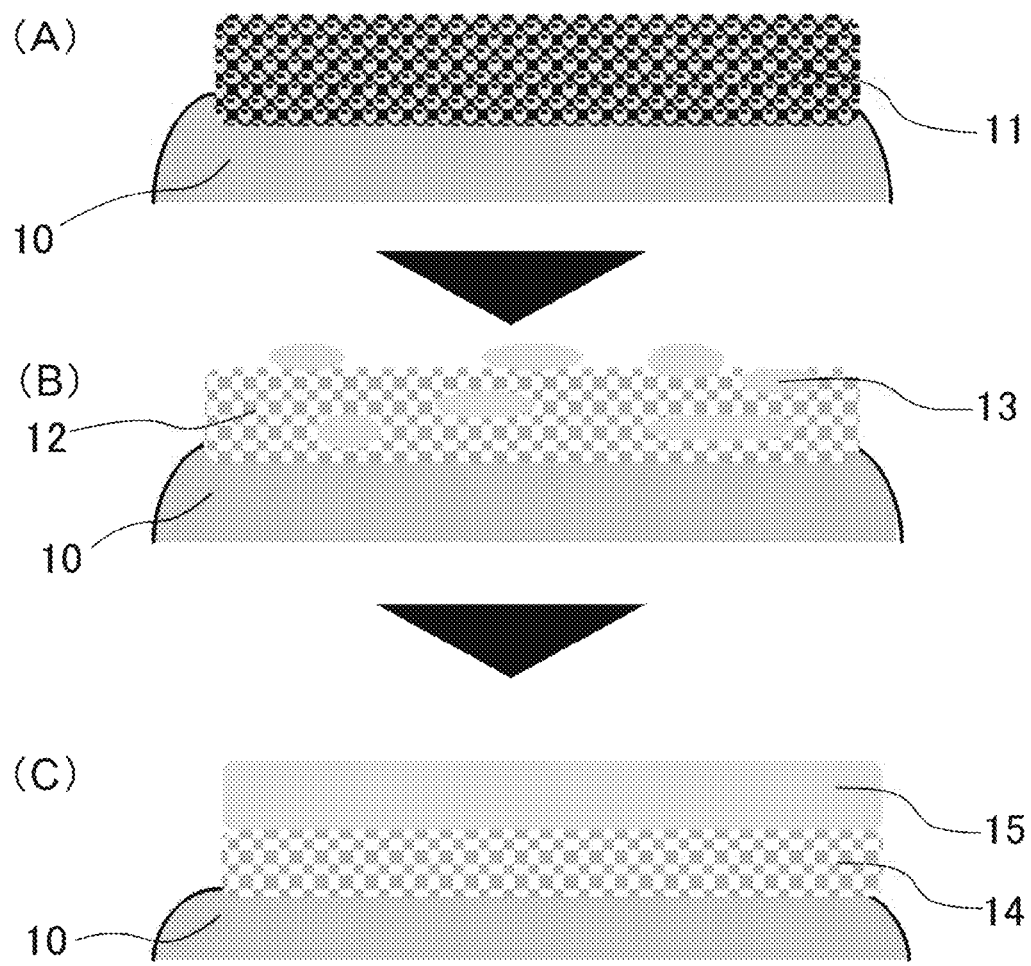
FIG. 2 shows the structural change of the composition after applying the water-in-oil emulsion composition of the present invention onto the skin.

FIG. 2 shows the change of the composition after applying the emulsion composition of the present invention to the skin.

FIG. 2 (A) is the state when the emulsion composition of the present invention is put onto skin 10, and shows the composition itself before application. At the point of FIG. 1 (A), components (a) to (d) constitute uniform layer 11 such as in FIG. 1 (A).

FIG. 2 (B) is the state of the emulsion composition of the present invention during application onto the skin. In the above-described composition, the emulsifying particles are dispersed and disintegrated by the shear of the composition being applied onto (spread over) the skin. As component (d) volatizes, component (b) and component (c) 13 separate from component (a) 12 that is adhered to the skin, and component (b) and component (c) 13 ooze out to the surface.

FIG. 2 (C) is the state after the application of the emulsion composition of the present invention onto the skin. The above-described component (a) has completely separated with components (b) and (c), and forms a double structure of adhesion layer 14 and transparent layer 15 respectively.

Adhesion layer 15 mainly comprised of component (b) provides glossy finish as an oil agent and, at the same time, contributes to the improvement of durability of makeup as a surface film by being fixed to component (c).

Component (a) also exhibits effect of gloss and the like as an oil agent. Additionally, as the component has a property of holding in coloring-materials, the above-described coloring-materials remain in adhesion layer 14 which is coated by the above-described transparent layer 15. Therefore, when coloring-materials are blended to the composition of the present invention, color-migration hardly occurs when the applied surface is touched.

Moreover, as transparent layer 15 of the surface promotes light dispersion, transparency like bare skin may be provided to the applied surface in the use of foundations and the like.

Depending on the combination of components (a) and (b), it may not separate into two layers completely as shown in FIG. 2 (C) after application to the skin. As shown in FIG. 2 (B), a film of components (b) and (c) may be formed partially on the film of component (a). In such case, the effect of the above-described double structure may be obtained sufficiently.

The manufacturing method of the emulsion composition of the present invention is not particularly limited, however, from the point of view of a preparation with stability, it is preferable to manufacture the composition to be a composition of uniform layer that components (a) and (b) are not separated within the composition. An example of such manufacturing method include a method comprising blending components (a) to (c) under heating to or above 90° C., adding component (d) which is heated to or above 90° C. under stirring for emulsion, and cooling as needed to form an emulsion composition of a uniform layer.

Furthermore, in the present invention, in addition to the components described above, the components that are normally used in cosmetics, external preparations for skin and the like such as oil agent other than the ones described above, wax, surfactant, coloring-material, powder, polymer compound, moisturizer, perfume, antioxidant agent, preservative, beauty component and the like may be blended within the range that the effect of the present invention is not impaired.

The water-in-oil emulsion composition of the present invention can be used as a base agent for a wide range of use such as cosmetics, external preparations for skin and the like, and in particular, exhibits feeling in use which is suitable as cosmetics.

Above all, application for cosmetics which is used by applying to the outer skin such as whitening essence, milky lotion, cream, pack, foundation, make-up base, lipstick, lip gloss, eye shadow, eye liner, mascara, hair dye, hair treatment, hair form, hair pack and the like are preferable, and especially, use in foundation is preferable.

The above-described components (a) to (d), as described above, may be used as one emulsion composition containing all components (a) to (d), or it may be used by separately preparing the component constituting the surface layer in the applied surface and the component constituting the transparent layer in the applied surface. In such use, a composition containing components (a) and (d) which constitute the surface layer is regarded as a first agent and a composition containing components (b) and (c) which constitute the transparent layer is regarded as a second agent, and it is preferable to apply the above-described second agent on the applied surface after applying the above-described first agent onto the skin. In the use of the above-described multi-agents, similar to the case when it is used as one emulsion composition, the coating film having the double structure of the adhesion layer and the transparent layer as shown in FIG. 2 (C) may be obtained.

EXAMPLES

The present invention will hereinafter be explained in further detail with reference to examples, however, the present invention is by no means limited by these examples. The blending quantity is expressed, unless otherwise specified, by mass %.

Prior to illustrating the examples, the evaluation methods of the composition for each test will be explained.

<Stability of Composition>

The state of each composition after storing still for 1 week in a thermostatic bath set at 50° C. is evaluated by the evaluation criteria described below.

(Evaluation Criteria)

○: Separation of the composition was not observed, and uniform layer state was maintained.

○Δ: Separation of the composition was hardly observed, and uniform layer state was almost maintained.

Δ: Slight separation of the composition was observed.

X: Remarkable separation of the composition was observed.

<Fresh Feeling in Use>

The actual usability test by 10 professional panelists was carried out. Each composition was scored on the basis of the below-described scores regarding fresh feeling in use, and the calculated score average values were evaluated by the below-described evaluation criteria as the evaluation values.

(Score)

5 points: Excellent
4 points: Good
3 points: Average
2 points: Poor
1 point: Extremely poor (Evaluation Criteria)

○: The evaluation value (average value) is 4.0 points or more and 5.0 points or less.

Δ: The evaluation value (average value) is 2.5 points or more and less than 4.0 points.

X: The evaluation value (average value) is 1.0 point or more and less than 2.5 points.

<Glossy Finish>

The actual usability test by 10 professional panelists was carried out. Each composition was scored on the basis of the below-described scores regarding glossy finish, and the calculated score average values were evaluated by the below-described evaluation criteria as the evaluation values.

(Score)

5 points: Excellent
4 points: Good
3 points: Average
2 points: Poor
1 point: Extremely poor (Evaluation Criteria)

○: The evaluation value (average value) is 4.0 points or more and 5.0 points or less.

Δ: The evaluation value (average value) is 2.5 points or more and less than 4.0 points.

X: The evaluation value (average value) is 1.0 point or more and less than 2.5 points.

<Excellence in Durability of Makeup>

The actual usability test by 10 professional panelists was carried out. Each composition was scored on the basis of the below-described scores regarding excellence in durability of makeup, and the calculated score average values were evaluated by the below-described evaluation criteria as the evaluation value.

(Score)
5 points: Excellent
4 points: Good
3 points: Average
2 points: Poor
1 point: Extremely poor
(Evaluation criteria)
◯: The evaluation value (average value) is 4.0 points or more and 5.0 points or less.
Δ: The evaluation value (average value) is 2.5 points or more and less than 4.0 points.
X: The evaluation value (average value) is 1.0 point or more and less than 2.5 points.

The composition of each test example was prepared in accordance with the formulations shown in the following Table 1, and blending of component (a) and component (b) was investigated on the basis of the above-described evaluations of stability, fresh feeling in use, glossy finish and excellence in durability of makeup. The results are shown in Table 1 below.

completely compatible with component (a), as component (b) became uniform as a composition having freshness by blending of water. However, as the oil component did not separate into 2 layers after application and the surface layer by silicone oil was not formed, the durability of makeup was poor.

Furthermore, in test example 1-7 which did not blend component (b), similar to test example 1-6, it became uniform as a composition and freshness as a water-in-oil emulsion composition was recognized. However, as the separated surface layer did not exist, the durability of makeup was poor.

From the above, in the present invention, it is preferable to use a polyhydric alcohol fatty acid ester or a hydrocarbon as component (a), and a transparent non-volatile silicone oil that separates when mixed with component (a) at 25° C. as component (b).

By the formulation shown below in Table 2, emulsion compositions of test examples 2-1 to 2-5, which contains various kinds of gelling agents, were prepared, and their stability was evaluated from the appearance of each com-

TABLE 1

|  | Test Example | | | | | | |
| --- | --- | --- | --- | --- | --- | --- | --- |
|  | 1-1 | 1-2 | 1-3 | 1-4 | 1-5 | 1-6 | 1-7 |
| Component (a) | | | | | | | |
| Polyglyceryl-5 triisostearate | 3 | — | — | — | — | 3 | 13 |
| Glyceryl monoisostearate | — | 3 | — | — | — | — | — |
| Pentaerythrityl tetra (behenate/benzoate/ethylhexanoate) (*1) | — | — | 3 | — | — | — | — |
| Dipenfaerythrityl hexahydroxystearate (*2) | — | — | — | 3 | — | — | — |
| Hydrogenated polyisobutene | — | — | — | — | 1 | — | — |
| Liquid paraffin | — | — | — | — | 2 | — | — |
| Component (b) | | | | | | | |
| Dimethicone (*3) | 10 | 10 | 10 | 10 | 10 | — | — |
| Polyglyceryl-2 triisostearate (*4) | — | — | — | — | — | 10 | — |
| Component (c) | | | | | | | |
| Zinc decyl trisiloxanecarboxylate | 1 | 1 | 1 | 1 | 1 | 1 | 1 |
| Component (d) | | | | | | | |
| Ion-exchanged water | Balance | Balance | Balance | Balance | Balance | Balance | Balance |
| Lauryl PEG-9 polydimethylsiloxyethyl dimethicone (*5) | 1 | 1 | 1 | 1 | 1 | 1 | 1 |
| Microcrystalline wax | 2 | 2 | 2 | 2 | 2 | 2 | 2 |
| Ethylhexyl methoxycinnamate | 3 | 3 | 3 | 3 | 3 | 3 | 3 |
| Foundation coloring-material lake | 17 | 17 | 17 | 17 | 17 | 17 | 17 |
| Stability of component (50° C.) | ◯ | ◯ | ◯ | ◯ | ◯ | ◯ | ◯ |
| Fresh feeling in use | ◯ | ◯ | ◯ | ◯ | ◯ | ◯ | ◯ |
| Glossy finish | ◯ | ◯ | ◯ | ◯ | ◯ | ◯ | ◯ |
| Excellence in durability of makeup | ◯ | ◯ | ◯ | ◯ | ◯ | X | X |

*1: SALACOS PB822 (manufactured by The Nisshin OilliO Group, Ltd.)
*2: COSMOL 168M (manufactured by The Nisshin OilliO Group, Ltd.)
*3: KF-96A-6cs (manufactured by Shin-Etsu Chemical Co., Ltd.)
*4: COSMOL 43V (manufactured by The Nisshin OilliO Group, Ltd.)
*5: KF-6038 (manufactured by Shin-Etsu Chemical Co., Ltd.)

(Manufacturing Method)
Components other than components (b) and (d) were added to component (a) and mixed until it became uniform under heating. The mixture was mixed with component (b) under heating. Component (d) was gradually added to the obtained mixture under heating and stirring, and a water-in-oil emulsion composition (foundation) was obtained.

As shown in Table 1, in the formulations of test examples 1-1 to 1-5 which used various polyhydric alcohol fatty acid esters or hydrocarbons as component (a), a stable creamy emulsion composition having fresh feeling in use was obtained. In addition, the applied surface separated into 2 layers, thus exhibiting glossy finish and excellence in durability of makeup.

On the other hand, test example 1-6 which blended polyglyceryl-2 triisostearate, which is an oil component position after storage. Appearance photographs of the compositions of test examples 2-1 to 2-5 after storing for 5 days under environment of 50° C. are shown in FIGS. 3A to 3E.

TABLE 2

| (Component) | (mass %) |
| --- | --- |
| Component (a) | |
| Polyglyceryl-5 triisostearate | 3 |
| Component (b) | |
| Dimethicone (*3) | 10 |

TABLE 2-continued

| (Component) | (mass %) |
|---|---|
| Component (c) | |
| Each gelling agent below | 1 |
| Component (d) | |
| Ion-exchanged water | Balance |
| Microcrystalline wax | 2 |
| Ethylhexyl methoxycinnamate | 3 |
| Foundation coloring-material lake | 17 |

(Manufacturing Method)

Components other than components (b) and (d) were added to component (a) and mixed until it became uniform under heating. The mixture was mixed with component (b) under heating. Component (d) was gradually added to the obtained mixture under heating and stirring, and a water-in-oil emulsion composition (foundation) was obtained.

<Gelling Agent>

Figure 3:
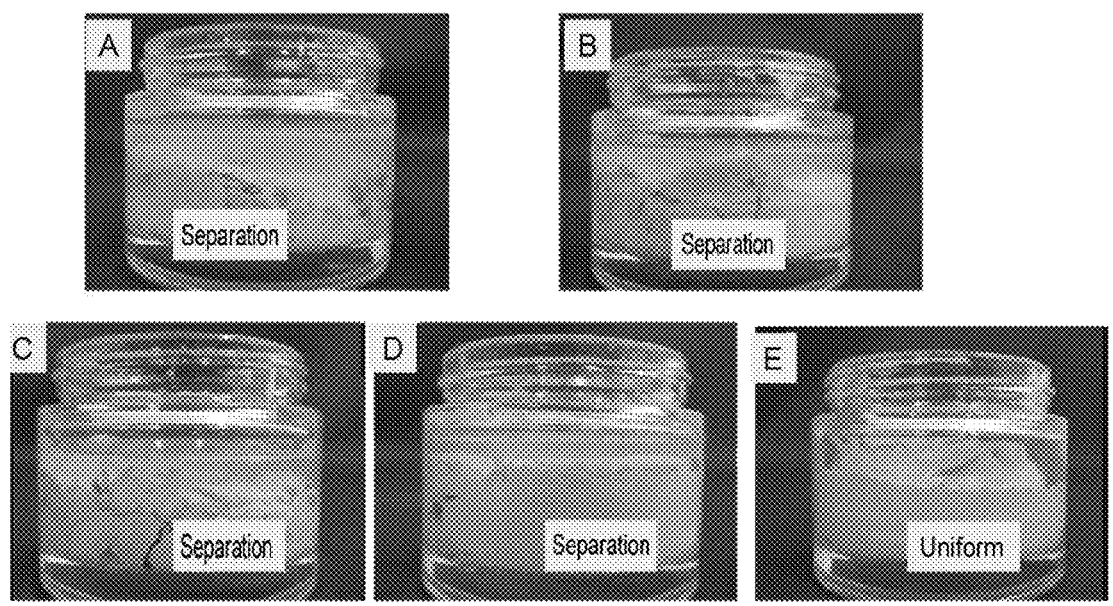
FIG. 3 shows the appearance of the composition when each gelling agent was used as component (c) in the water-in-oil emulsion composition of the present invention.

Test example 2-1 (FIG. 3 A): Gelling agent was not blended (ion-exchanged water)
Test example 2-2 (FIG. 3 B): Dextrin palmitate
Test example 2-3 (FIG. 3 C): Glyceryl (behenate/eicosadioate)
Test example 2-4 (FIG. 3 D): Microcrystalline wax 7: paraffin 93 or microcrystalline wax (PARMIC 160, manufactured by Nikko Rica Corporation)
Test example 2-5 (FIG. 3 E): Zinc decyl trisiloxanecarboxylate As shown in FIG. 3, in any of the compositions of test examples other than test example 2-5 which used zinc decyl trisiloxane carboxylate, the oil agents separated and the state of uniform layer was not maintained.

Therefore, in the water-in-oil emulsion composition of the present invention, it is preferable to blend zinc decyl trisiloxanecarboxylate to maintain a stable state that the oil agents which separate with each other are uniformly dispersed.

Examples of the present invention are given below, but the present invention is not limited thereto. Compositions of any formulation examples maintained excellent stability (50° C. 1 W) and exhibited fresh feeling in use, glossy finish and excellent durability of makeup.

Examples 1~6

Foundation

| Component | Example 1 | Example 2 | Example 3 | Example 4 | Example 5 | Example 6 |
|---|---|---|---|---|---|---|
| (1) Polyglyceryl-5 triisostearate | | 1 | 2 | | 1 | 2 |
| (2) Pentaerythrityl tetra (behenate/benzoate/ethylhexanoate)(*2) | 3 | 2 | 1 | 3 | 2 | 1 |
| (3) Dimethicone(*3) | 10 | 10 | 10 | 10 | 10 | 10 |
| (4) Zinc decyl trisiloxanecarboxylate | 1 | 1 | 1 | 1 | 1 | 1 |
| (5) Ion-exchanged water | Balance | Balance | Balance | Balance | Balance | Balance |
| (6) Lauryl PEG-9polydimethylsiloxyethyl dimethicone(*5) | 1 | 1 | 1 | | | |
| (7) PEG-10 dimethicone(*6) | | | | 1 | 1 | 1 |
| (8) Microcrystalline wax | 2 | 2 | 2 | 2 | 2 | 2 |
| (9) Ethylhexyl methoxycinnamate | 3 | 3 | 3 | 3 | 3 | 3 |
| (10) Foundation coloring-material lake | 17 | 17 | 17 | 17 | 17 | 17 |
| (11) Hydrophobized black iron oxide | | 0.06 | 0.06 | 0.06 | 0.06 | 0.06 |
| (12) Hydrophobized titanium oxide | | 9 | 9 | 9 | 9 | 9 |

*6: KF-6017 (manufactured by Shin-Etsu Chemical Co., Ltd.)

(Manufacturing Method)

Components other than (3) and (5) were added to (1) and (2) and mixed until it became uniform under heating. The mixture was mixed with (3) under heating. (5) was gradually added to the obtained mixture under heating and stirring, and a water-in-oil emulsion composition (foundation) was obtained.

Examples 7~12

Emulsion Pact (Emulsion Foundation)

| Component | Example 7 | Example 8 | Example 9 | Example 10 | Example 11 | Example 12 |
|---|---|---|---|---|---|---|
| (1) Zinc decyl trisiloxanecarboxylate | 1 | 1 | 1 | 1 | 1 | 1 |
| (2) Glyceryl monoisostearate | | | | | 1 | 1 |
| (3) Polyglyceryl-5 triisostearate | 1 | 1 | 1 | 1 | | |
| (4) Pentaerythrityl tetra (behenate/benzoate/ethylhexanoate) | 2 | 2 | 2 | 2 | 2 | 2 |
| (5) Dimethicone | 8 | 8 | 8 | 13 | 8 | 8 |
| (6) Cyclomethicone | 16.8 | 23.8 | 26.8 | 30.87 | 23.8 | 26.8 |
| (7) Isohexadecane | 7 | | | | | |
| (8) Paraffin wax | 4 | 4 | 4 | 4 | 4 | 4 |
| (9) Microcrystalline wax | 0.9 | 0.9 | 0.9 | 0.9 | 0.9 | 0.9 |

-continued

| Component | Example 7 | Example 8 | Example 9 | Example 10 | Example 11 | Example 12 |
|---|---|---|---|---|---|---|
| (10) Distearyldimethylammonium chloride | 0.2 | 0.2 | 0.2 | 0.2 | 0.2 | 0.2 |
| (11) Palmitic acid | 0.15 | 0.15 | 0.15 | 0.15 | 0.15 | 0.15 |
| (12) PEG-10 dimethicone | 2.5 | 2.5 | | 2.5 | 2.5 | |
| (13) Sorbitan sesquiisostearate | 0.5 | 0.5 | | 0.5 | 0.5 | |
| (14) Hydrophobized titanium oxide | 9 | 9 | 9 | 12 | 9 | 9 |
| (15) Hydrophobized yellow iron oxide | 2.37 | 2.37 | 2.37 | 3.081 | 2.37 | 2.37 |
| (16) Hydrophobized red iron oxide | 0.67 | 0.67 | 0.67 | 0.871 | 0.67 | 0.67 |
| (17) Hydrophobized black iron oxide | 0.06 | 0.06 | 0.06 | 0.078 | 0.06 | 0.06 |
| (18) Fine particle titanium oxide | 7 | 7 | 7 | 7 | 7 | 7 |
| (19) Spherical silica | 3 | 3 | 3 | 10 | 3 | 3 |
| (20) Ion-exchanged water | 30 | 30 | 30 | 7 | 30 | 30 |
| (21) Dipropylene glycol | 3.5 | 3.5 | 3.5 | 3.5 | 3.5 | 3.5 |
| (22) Phenoxy ethanol | 0.35 | 0.35 | 0.35 | 0.35 | 0.35 | 0.35 |

(Manufacturing Method)

(1) to (4) and (7) to (19) were mixed under heating. The mixture was added to a mixture of (5) and (6) which was mixed and heated separately, and mixed until it became uniform under heating. Then, a mixed solution of (20) to (22) was gradually added to the above-described mixture under heating and stirring, and a water-in-oil emulsion composition (emulsion foundation) was obtained.

Examples 13~16

Liquid Foundation

| Component | Example 13 | Example 14 | Example 15 | Example 16 |
|---|---|---|---|---|
| (1) Glyceryl monoisostearate | 1 | | 1.4 | |
| (2) Isostearyl glyceryl ether | | | | 1.4 |
| (3) Pentaerythrityl tetra (behenate/benzonate/ ethylhexanoate) | 2 | | | |
| (4) Dipentaerythrityl hexahydroxystearate | | 3 | | |
| (5) Dimethicone | 8 | 5 | 5 | 5 |
| (6) Cyclomethicone | 11.3 | 5 | 11.3 | 11.3 |
| (7) Isohexadecane | | 5 | | |
| (8) Zinc decyl trisiloxanecarboxylate | 1 | 3 | 1 | 1 |
| (9) Lauryl PEG-9poly-dimethylsiloxyethyl dimethicone | 0.5 | | 0.5 | 0.5 |
| (10) 2-ethylhexyl parametoxycinnamate | 3 | | 3 | 3 |
| (11) Isostearic acid | 0.5 | | 0.5 | 0.5 |
| (12) PEG-10 dimethicone | 0.5 | 0.5 | 0.5 | 0.5 |
| (13) Fine particle titanium oxide | 5 | 5 | 5 | 5 |
| (14) Hydrophobized titanium oxide | 9 | 9 | 9 | 9 |
| (15) Hydrophobized red iron oxide | 0.84 | 0.84 | 0.84 | 0.84 |
| (16) Hydrophobized yellow iron oxide | 2.62 | 2.62 | 2.62 | 2.62 |
| (17) Hydrophobized black iron oxide | 0.29 | 0.29 | 0.29 | 0.29 |
| (18) Spherical powder | 1.33 | | 1.33 | 1.33 |
| (19) Glycerin | 5 | 4 | 5 | 5 |
| (20) 1,3-butylene glycol | 5 | 5 | 5 | 5 |
| (21) Paraben | 0.25 | 0.25 | 0.25 | 0.25 |
| (22) Salt | | | 1 | 1 |

-continued

| Component | Example 13 | Example 14 | Example 15 | Example 16 |
|---|---|---|---|---|
| (23) Ion-exchanged water | 42.57 | 51.2 | 46.17 | 46.17 |
| (24) Phenoxy ethanol | 0.3 | 0.3 | 0.3 | 0.3 |

(Manufacturing Method)

(1) to (4) and (7) to (18) were mixed under heating. The mixture was added to a mixture of (5) and (6) which was mixed and heated separately, and mixed until it became uniform under heating. Then, a mixed solution of (19) to (24) was gradually added to the above-described mixture under heating and stirring, and an emulsion composition (liquid foundation) was obtained.

Example 17

Liquid Foundation

| (Component) | (mass %) |
|---|---|
| (1) Polyglyceryl-5 triisostearate | 15 |
| (2) Cyclomethicone (KF-995, manufactured by Shin-Etsu Silicone Co., Ltd.) | 4.38 |
| (3) Dimethicone (KF-96A-6cs, manufactured by Shin-Etsu Chemical Co., Ltd) | 5 |
| (4) Zinc decyl trisiloxanecarboxylate | 3 |
| (5) Sorbitan sesquiisostearate (ESTEMOL 182V, manufactured by The Nisshin OilliO Group, Ltd.) | 2 |
| (6) Hydrophobized titanium oxide | 20.7 |
| (7) Hydrophobized yellow iron oxide | 4 |
| (8) Hydrophobized red iron oxide | 0.84 |
| (9) Pearlescent agent | 8 |
| (10) Ion-exchanged water | Balance |

(Manufacturing Method)

(1) and (4) to (9) were mixed under heating. The mixture was added to a mixture of (2) and (3) which was mixed and heated separately, and mixed until it became uniform under heating. Then, (10) was gradually added to the above-described mixture under heating and stirring, and an emulsion composition (liquid foundation) was obtained.

Example 18

Eye Shadow

| (Component) | (mass %) |
| --- | --- |
| (1) Polyglyceryl-5 triisostearate | 15 |
| (2) Cyclomethicone (KF-995, manufactured by Shin-Etsu Silicone Co., Ltd.) | 10 |
| (3) Dimethicone (KF-96A-6cs, manufactured by Shin-Etsu Chemical Co., Ltd) | 5 |
| (4) Zinc decyl trisiloxanecarboxylate | 3 |
| (5) Sorbitan sesquiisostearate (ESTEMOL 182V, manufactured by The Nisshin OilliO Group, Ltd.) | 2 |
| (6) Hydrophobized yellow iron oxide | 0.32 |
| (7) Hydrophobized titanium oxide (pink) | 0.1 |
| (8) Hydrophobized titanium oxide (green) | 0.8 |
| (9) Hydrophobized pearlescent agent (PROMINENCE SF, manufactured by Topy Industries, Ltd.) | 2 |
| (10) Hydrophobized pearlescent agent (TIMIRON MP-115, manufactured by Merck Ltd.) | 3 |
| (11) Hydrophobized pearlescent agent (TIMIRON SPLENDED GREEN, manufactured by Merck Ltd.) | 5 |
| (12) Hydrophobized pearlescent agent (TIMIRON MP-45, manufactured by Merck Ltd.) | 10 |
| (13) Pearlescent agent (XIRONA MAGIC MAUVE, manufactured by Merck Ltd.) | 0.1 |
| (14) Ion-exchanged water | Balance |

(Manufacturing Method)

(1) and (4) to (13) were mixed under heating. The mixture was added to a mixture of (2) and (3) which was mixed and heated separately, and mixed until it became uniform under heating. Then, (14) was gradually added to the above-described mixture under heating and stirring, and an emulsion composition (eye shadow) was obtained.

Example 19

Temporary Hair Dyeing Agent

| (Component) | (mass %) |
| --- | --- |
| (1) Polyglyceryl-5 triisostearate | 15 |
| (2) Cyclomethicone (KF-995, manufactured by Shin-Etsu Silicone Co., Ltd.) | 10 |
| (3) Diphenylsiloxy phenyl trimethicone (Silicone KF56, manufactured by Shin-Etsu Silicone Co., Ltd) | 5 |
| (4) Zinc decyl trisiloxanecarboxylate | 3 |
| (5) Microcrystalline wax 7: Paraffin 93 or Microcrystalline wax (PARMIC 160, manufactured by Nikko Rica Corporation) | 2 |
| (6) Sorbitan sesquiisostearate (ESTEMOL 182V, manufactured by The Nisshin OilliO Group, Ltd.) | 2 |
| (7) Hydrophobized black iron oxide | 8 |
| (8) Metal soap-treated talc | 7 |
| (9) Ion-exchanged water | Balance |

(Manufacturing Method)

(1) and (4) to (8) were mixed under heating. The mixture was added to a mixture of (2) and (3) which was mixed and heated separately, and mixed until it became uniform under heating. Then, (9) was gradually added to the mixture under heating and stirring, and an emulsion composition (temporary hair dyeing agent) was obtained.

Example 20

Mascara

| (Component) | (mass %) |
| --- | --- |
| (1) Glyceryl monoisostearate | 1.4 |
| (2) Polyglyceryl triisostearate | 5 |
| (3) Pentaerythrityl tetra(behenate/benzonate/ethylhexanoate) | 5 |
| (4) Zinc decyl trisiloxanecarboxylate | 3 |
| (5) Trimethylsiloxysilicate | 10 |
| (6) Cyclomethicone | 14.45 |
| (7) Methylphenylpolysiloxane | 3 |
| (8) Microcrystalline wax | 2 |
| (9) Paraffin wax | 6 |
| (10) Hydrophobized black iron oxide | 10 |
| (11) 1,3-Butylene glycol | 5 |
| (12) Methylparaben | 0.15 |
| (13) Mixture of acrylic alkyl copolymer emulsion (2) | 10 |
| (14) Polyvinyl alcohol | 10 |
| (15) Ion-exchanged water | 15 |

(Manufacturing Method)

(1) to (5) and (8) to (10) were mixed under heating. The mixture was added to a mixture of (6) and (7) which was mixed and heated separately, and mixed until it became uniform under heating. Then, a mixed solution of (11) to (15) was gradually added to the above-described mixture under heating and stirring, and an emulsion composition (mascara) was obtained.

Example 21

Lipstick

| (Component) | (mass %) |
| --- | --- |
| (1) Glyceryl monoisostearate | 1.4 |
| (2) Polyglyceryl triisostearate | 13.6 |
| (3) Pentaerythrityl tetra(behenate/benzonate/ethylhexanoate) | 5 |
| (4) Zinc decyl trisiloxanecarboxylate | 3 |
| (5) Trimethylsiloxysilicate | 10 |
| (6) Diphenyl dimethicone | 5 |
| (7) Methyl phenyl trisiloxane | 5 |
| (8) Coloring-material lake | 6 |
| (9) Pearlescent agent | 3 |
| (10) PEG-10 dimethicone | 1 |
| (11) Water | 36 |
| (12) Glycerin | 5 |
| (13) Paraffin wax | 3 |
| (14) Isohexadecane | 3 |

(Manufacturing Method)

(1) to (5), (8) to (10), (13) and (14) were mixed under heating. The mixture was added to a mixture of (6) and (7) which was mixed and heated separately, and mixed until it became uniform under heating. Then, a mixed solution of (11) and (12) was gradually added to the above-described mixture under heating and stirring, and an emulsion composition (lipstick) was obtained.

DESCRIPTION OF REFERENCE NUMBERS

1 Component (c)
2 Component (d)
3 Component (b)

4 Lamella of component (a) and component (d)
10 Skin
11 Uniform layer
12 Component (a)
13 Component (b)
14 Adhesion layer
15 Transparent layer

What is claimed is:

1. A water-in-oil emulsion composition comprising:
   (a) 1 to 20 mass % of a polyhydric alcohol fatty acid ester, wherein the polyhydric alcohol fatty acid ester is selected from the group consisting of polyglyceryl isostearate, glyceryl monoisostearate, pentaerythritol fatty acid ester, and isostearyl glyceryl ether;
   (b) 3 to 20 mass % of a transparent non-volatile silicone oil that separates when mixed with component (a) at 25° C.;
   (c) 0.1 to 5 mass % of zinc decyl trisiloxanecarboxylate; and
   (d) water.

2. The water-in-oil emulsion composition according to claim 1, wherein the addition mole number of glycerin of component (a) is 4 to 10 and the number of isostearic acid residues of component (a) is 1 to 4.

3. The water-in-oil emulsion composition according to claim 1, wherein the water-in-oil emulsion composition comprising the components (a), (b), (c) and (d) further comprises (e) a silicone surfactant having an HLB value of 7 or less.

4. A cosmetic comprising the water-in-oil emulsion composition according to claim 1.

5. A makeup method comprising:
   (I) applying a first agent containing a polyhydric alcohol fatty acid ester, wherein the polyhydric alcohol fatty acid ester is selected from the group consisting of polyglyceryl isostearate, glyceryl monoisostearate, pentaerythritol fatty acid ester, and isostearyl glyceryl ether and water; and
   (II) applying a second agent containing a transparent non-volatile silicone oil that separates when mixed with the polyhydric alcohol fatty acid ester at 25° C. and zinc decyl trisiloxanecarboxylate on the applied surface after process (I).

6. A cosmetic comprising the water-in-oil emulsion composition according to claim 2.

7. A cosmetic comprising the water-in-oil emulsion composition according to claim 3.

* * * * *